United States Patent
Daniel

(10) Patent No.: US 9,554,908 B2
(45) Date of Patent: Jan. 31, 2017

(54) METHOD AND A KIT OF PARTS FOR IMPLANTING A PENILE PROSTHETIC INSERT

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 80 days.

(21) Appl. No.: 14/554,062

(22) Filed: Nov. 26, 2014

(65) Prior Publication Data

US 2016/0089210 A1    Mar. 31, 2016

Related U.S. Application Data

(60) Provisional application No. 62/057,570, filed on Sep. 30, 2014.

(51) Int. Cl.
*A61F 2/26* (2006.01)
*A61B 19/00* (2006.01)
*A61B 19/02* (2006.01)

(52) U.S. Cl.
CPC .............. *A61F 2/26* (2013.01); *A61B 19/026* (2013.01); *A61B 19/22* (2013.01); *A61B 19/46* (2013.01); *A61B 34/73* (2016.02); *A61B 2019/0278* (2013.01); *A61B 2019/2257* (2013.01); *A61B 2019/461* (2013.01); *A61F 2210/009* (2013.01); *A61F 2220/0008* (2013.01); *A61F 2250/0001* (2013.01); *A61F 2310/00035* (2013.01)

(58) Field of Classification Search
CPC ..... A61F 2/26; A61B 17/02; A61B 17/22031; A61B 17/0281; A61B 2090/3904; A61B 2017/00876
USPC .............................. 600/38–41; 128/898, 899
See application file for complete search history.

(56) References Cited

U.S. PATENT DOCUMENTS

| | | | |
|---|---|---|---|
| 7,766,810 B2* | 8/2010 | Ohdaira | A61B 17/02 128/899 |
| 8,316,861 B2* | 11/2012 | Brewer | A61B 1/00158 128/899 |
| 2011/0174313 A1 | 7/2011 | Von Pechmann et al. | |
| 2011/0184440 A1 | 7/2011 | Saldinger | |

FOREIGN PATENT DOCUMENTS

| | | |
|---|---|---|
| EP | 0532162 A1 | 3/1993 |
| WO | 2004045421 A1 | 6/2004 |

\* cited by examiner

*Primary Examiner* — Samuel Gilbert
(74) *Attorney, Agent, or Firm* — Coloplast Corp., Coloplast A/S; Nick Baumann

(57) ABSTRACT

A method for implanting a penile prosthetic insert in a corpora cavernosum of a penis and engaging a first magnetic unit with an inflatable penile prosthetic cylinder. The method includes locating a second magnetic unit outside the penis and attracting the first magnetic unit through tissue of the penis with the second magnetic unit to effect moving of the first magnetic unit and the inflatable penile prosthetic cylinder inside the corpora cavernosum. Also disclosed is a kit of parts for implanting a penile prosthetic insert in a corpora cavernosum of a penis including a first magnetic unit and a second magnetic unit for delivering an inflatable penile prosthetic cylinder into the corpora cavernosum of the penis.

20 Claims, 15 Drawing Sheets

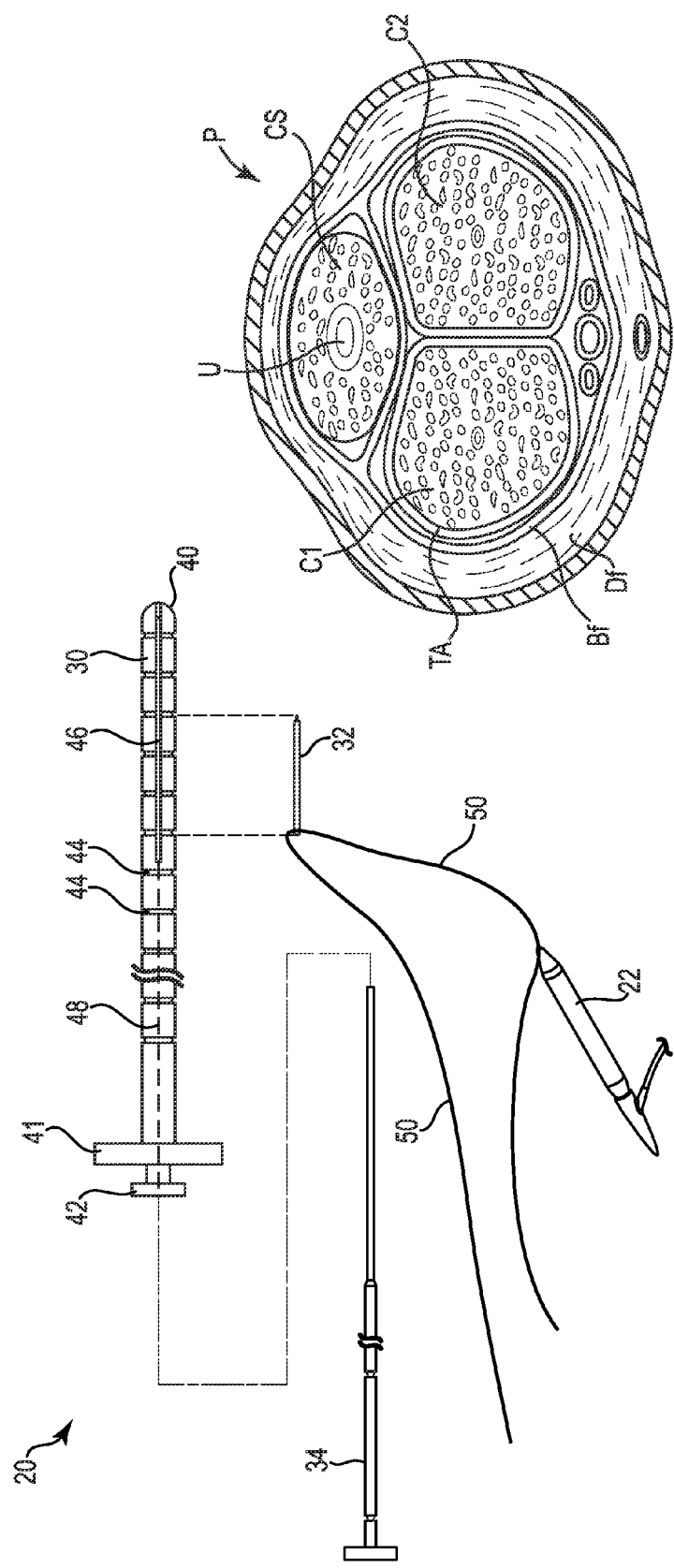

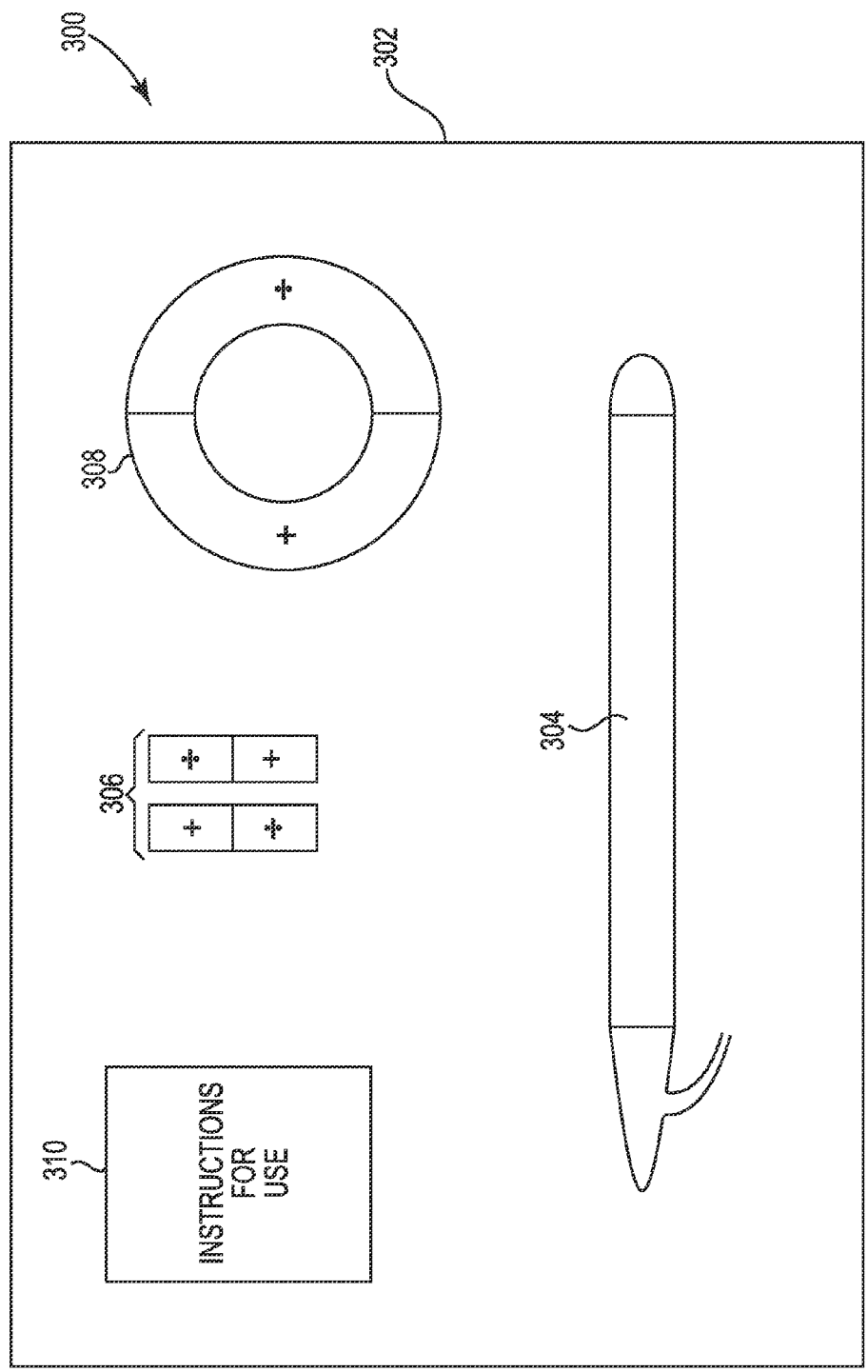

METHOD AND A KIT OF PARTS FOR IMPLANTING A PENILE PROSTHETIC INSERT

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a method for implanting a penile prosthetic insert in a corpora cavernosum of a penis. The method includes engaging a first magnetic unit with an inflatable penile prosthetic cylinder. The method includes forming an incision to access the corpora cavernosum. The method includes inserting the first magnetic unit and a distal tip portion of the inflatable penile prosthetic cylinder into the corpora cavernosum through the incision. The method includes locating a second magnetic unit outside the penis. The method includes attracting the first magnetic unit through tissue of the penis with the second magnetic unit. The method includes moving the second magnetic unit in a distal direction along an exterior surface of the penis to effect moving of the first magnetic unit and the inflatable penile prosthetic cylinder in the distal direction inside the corpora cavernosum. The method includes locating the distal tip portion of the inflatable penile prosthetic cylinder at a distal end of the corpora cavernosum.

One aspect provides a kit of parts for implanting a penile prosthetic insert in a corpora cavernosum of a penis. The kit of parts includes a packaging, an inflatable penile prosthetic cylinder, a first magnetic unit, a second magnetic unit and a set of instructions for employing the second magnetic unit to deliver the first magnetic unit and the inflatable penile prosthetic cylinder into the corpora cavernosum of the penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view of a prior art tool for implanting a cylinder into a penis illustrated in FIG. 1B.

FIG. 15 is a top view of one embodiment of a kit of parts.

DETAILED DESCRIPTION

Figure 1C:
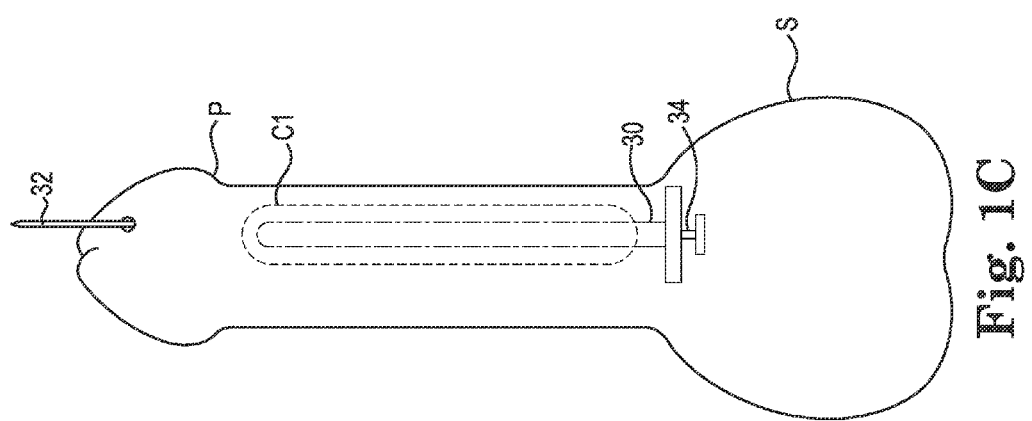
FIG. 1C is a schematic top view of a penis where the prior art tool is generally located within a corpora cavernosum of a penis and a needle penetrates through the glans penis.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

A typical penile prosthetic includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Embodiments provide a method of implanting a penile prosthetic cylinder in a corpora cavernosum of a penis using first and second magnetic units to introduce and position the cylinder in the corpora cavernosum. The first magnetic unit is engaged with the cylinder and is introduced with the cylinder into the corpora cavernosum. The second magnetic unit is provided outside the penis and is used for attracting and moving the first magnetic unit and the cylinder through tissue of the penis. The method is useful to avoid using a sharp needle to penetrate the glans penis for placement of a penile prosthetic insert.

Embodiments provide a kit of parts for implanting a penile prosthetic insert in a corpora cavernosum of a penis including first and second magnetic units.

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and a plunger 34 that is insertable into the barrel 30 to push the needle 32 out of the barrel 30.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the plunger 34.

The needle 32 is attached to a tow suture 50 that is coupled with the cylinder 22. The tow suture 50 is generally inserted through an eyelet of the needle 50 and a hole provided at a distal end of the cylinder 22.

The plunger 34 is insertable into the lumen 48 at the proximal end 42 of the barrel 30 and operates to push the needle 32 out of the lumen 48.

FIG. 1B is a cross-sectional view of the penis P oriented to access by the surgeon. The surgeon gains access to the corpora cavernosa though small incisions, and with this in mind, the cross-sectional view of FIG. 1B is not the view observed by the surgeon. In the view of FIG. 1B the penis P of the patient is reclined against the torso such that the urethra U, surrounded by corpus spongiosum tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the plunger 34 is inserted into the lumen 48 via the proximal end 42 of the barrel 30. The barrel 30 is inserted into the dilated corpora cavernosum and the plunger 34 is pushed into the lumen 48 to push the needle 32 out of the barrel 30 and through the glans penis. This is illustrated in the schematic top view of FIG. 1C showing a patient's penis as it would look to a surgeon when the penis is reclined against the patient's abdominal region (i.e. with the urethra oriented upward similar to FIG. 1B). The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

Pushing the needle 32 through the glans penis can cause bleeding from the head of the penis, which can be alarming to the patient. Surgeons have expressed a desire to avoid the use of the needle 32.

As noted above, the suture 50 is inserted through the distal, leading end of the cylinder 22. The distal end of the cylinder is oftentimes reinforced to accommodate the hole that the suture 50 is passed through. The reinforced end of the cylinder can be felt by some patients who perceive it as a hard and unnatural pointed projection.

Figure 2A:
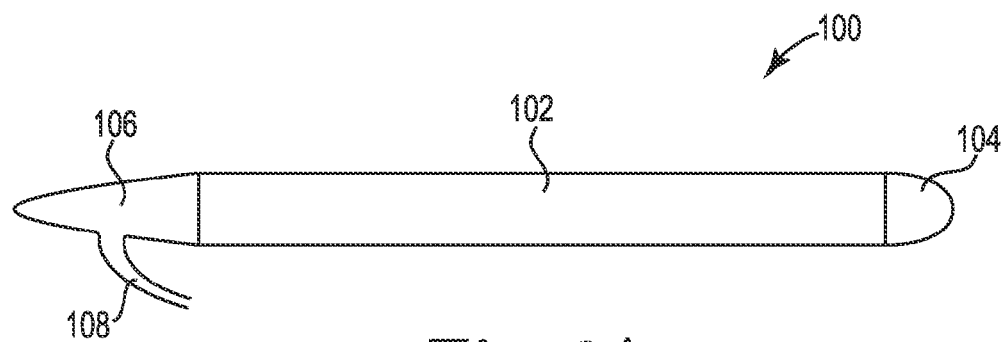
FIG. 2A is a side view of one example of an inflatable penile prosthetic cylinder for implantation into a corpora cavernosum of a penis.

FIG. 2A is a side view of one example of a penile prosthetic insert for implantation into a corpora cavernosum of a penis to restore erectile function, the insert configured as an inflatable penile prosthetic cylinder 100. The cylinder 100 includes an inflatable body portion 102 attached to a distal tip portion 104 and to a proximal tip portion 106. In one example tubing 108 extends from the proximal tip portion 106.

Figure 2B:
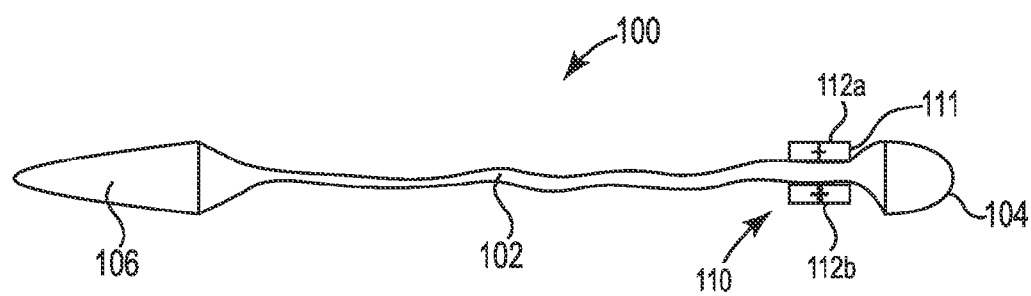
FIG. 2B is a top view of the inflatable cylinder of FIG. 2A in a deflated state and with a first magnetic unit engaged with the cylinder according to one embodiment of a method of implanting a penile prosthetic insert in a corpora cavernosum of a penis.

FIG. 2B is a top view of the inflatable cylinder 100 wherein the inflatable body portion 102 is in a deflated state and a first magnetic unit 110 is engaged with the cylinder 100 according to one embodiment of a method of implanting a penile prosthetic insert in a corpora cavernosum of a penis. In one embodiment, the first magnetic unit 110 includes mutually attracting magnet halves 112a, 112b engaged with each other on opposite sides of the inflatable body cylinder 100 to hold or clamp a portion of the cylinder 100 between the magnet halves 112a, 112b. Poles of the magnet halves facing away from the cylinder 100 are indicated with '+' (plus) and '÷' (minus) signs. In one embodiment, the first magnetic unit 110 is engaged with the inflatable cylinder 100 adjacent the distal end portion 104 such that a distal most end 111 of the first magnetic unit 110 is within 0-1.25 inches (0-32 mm) from the attachment of the distal end portion 104 to the inflatable body portion 102.

Figure 2C:
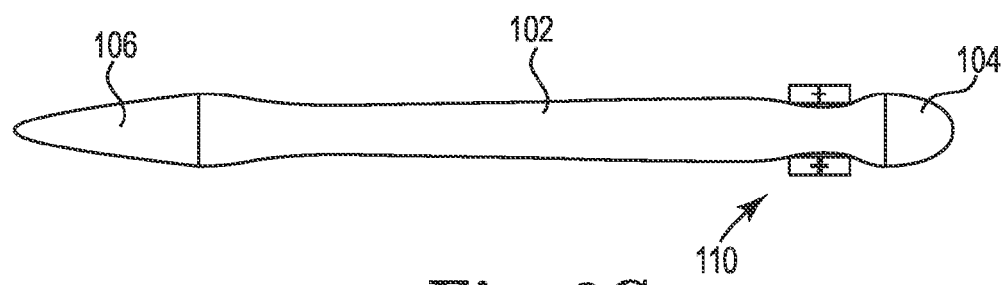
FIG. 2C is a side view of one embodiment wherein a first magnetic unit is engaged with an inflatable cylinder and wherein the cylinder is partially inflated.

FIG. 2C is a side view of one embodiment wherein the first magnetic unit 100 is engaged with the cylinder 100 and wherein the cylinder 100 is partially inflated. In embodiments, a partial inflation of the cylinder 100 helps provide control of the cylinder 100 during insertion into the corpora cavernosum because the partial inflation provides additional column strength of the cylinder. In one embodiment, the partial inflation can be done by injecting a liquid such as, but not limited to, a saline solution into the inflatable cylinder 100 via the tubing 108 (FIG. 2A) and temporarily holding the liquid inside the cylinder 100 during insertion into the corpora cavernosum.

Figure 3:
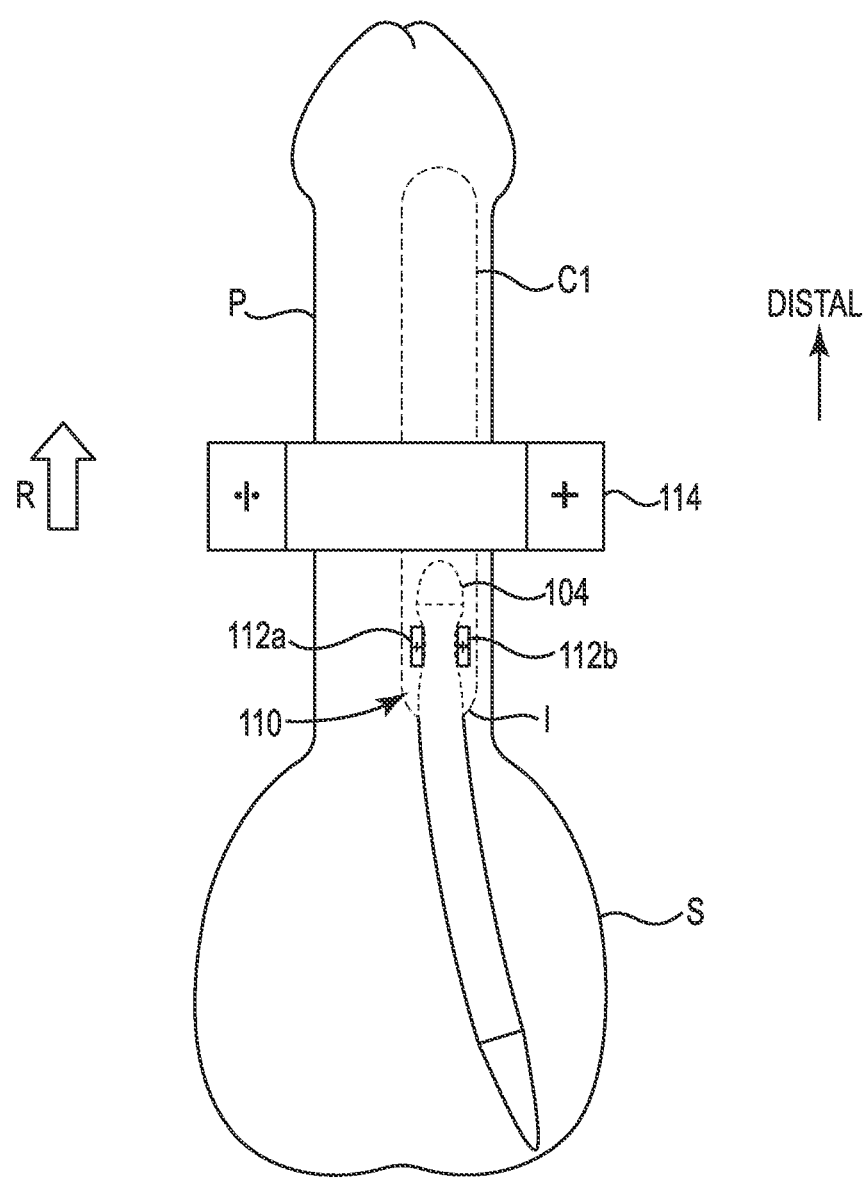
FIG. 3 is a schematic top view according to one embodiment wherein a first magnetic unit and a distal tip portion of a cylinder is inserted into the corpora cavernosum of a penis and a second magnetic unit is located outside the penis.

FIG. 3 is a schematic top view similar to FIG. 1C of a patient's penis P. According to one embodiment of the method, an incision I is formed to access a corpora cavernosum and the first magnetic unit 110 and the distal tip portion 104 of the cylinder 100 is inserted through the incision I into the corpora cavernosum C1 of the penis P, as illustrated in FIG. 3. In one embodiment, a second magnetic unit 114 is located outside the penis P. In one embodiment, the second magnetic unit 114 is sized to locate around the penis P providing a space between the second magnetic unit 114 and an exterior surface of the penis P. In one embodiment, the second magnetic unit 114 is configured as a ring. The second magnetic unit 114 attracts the first magnetic unit 110 through tissue of the penis P. In one embodiment, moving the second magnetic unit 114 (indicated by arrow R) in a distal direction along an exterior surface of the penis P effects moving the first magnetic unit 110 and the inflatable cylinder 100 in the distal direction inside the corpora cavernosum.

Figure 4:
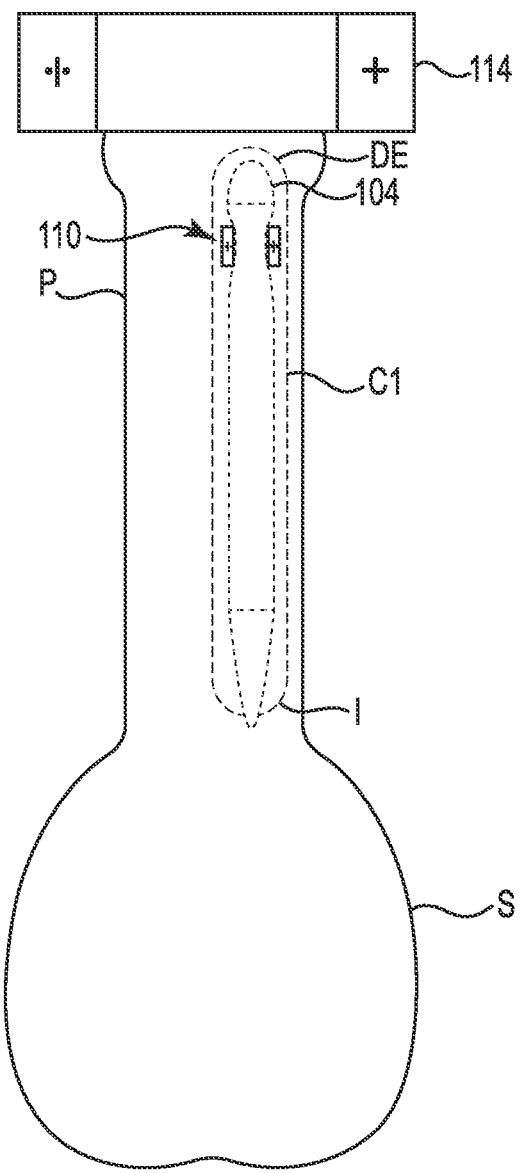
FIG. 4 is schematic top view illustrating one embodiment of the method including moving a first magnetic unit and a cylinder in a distal direction with a second magnetic unit.
Figure 5:
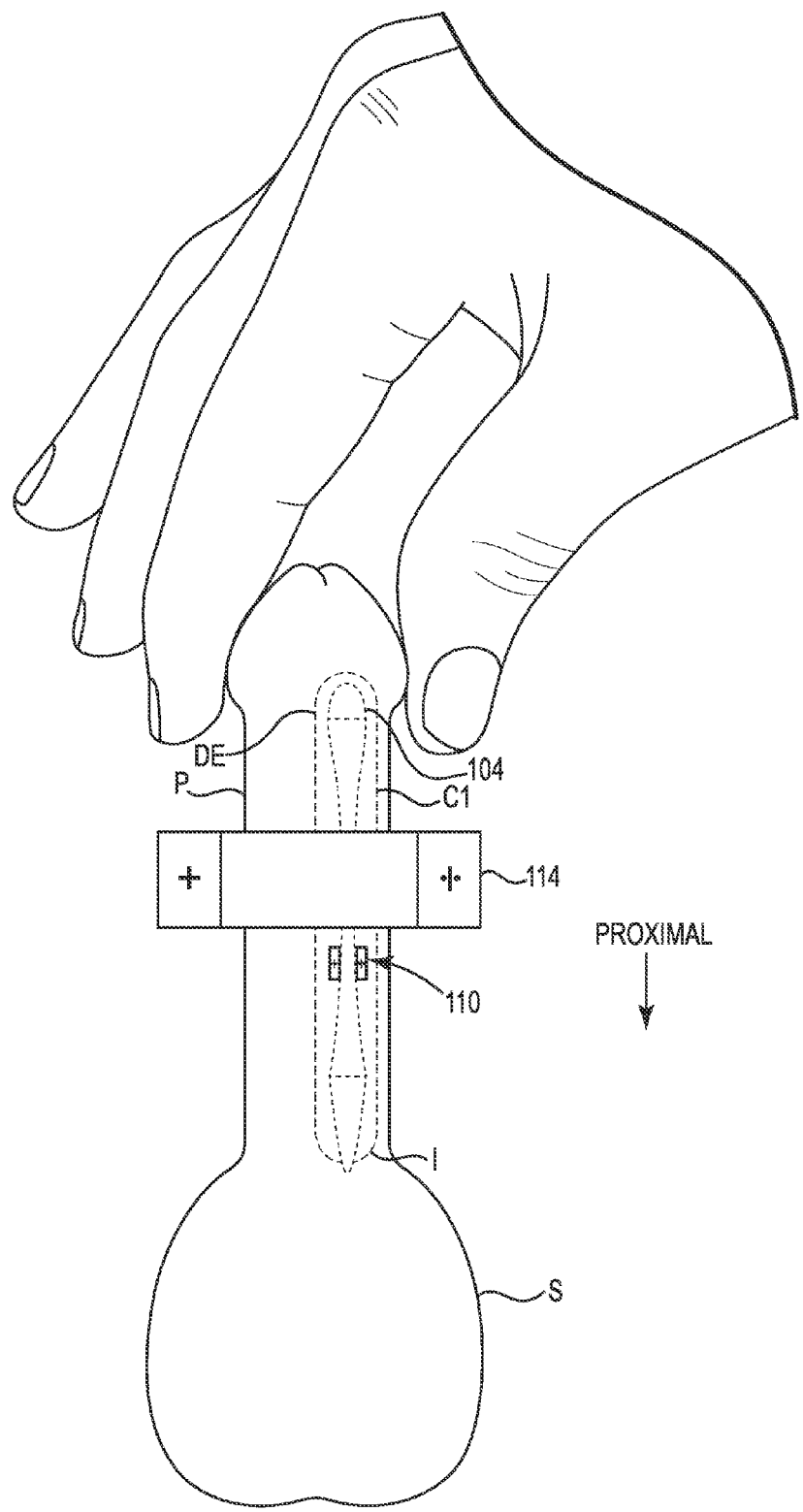
FIG. 5 is schematic top view illustrating one embodiment of the method including retaining a distal tip portion of an inflatable cylinder and moving a first magnetic unit in a proximal direction with a second magnetic unit.

FIG. 4 is schematic top view similar to FIG. 3 illustrating one embodiment of the method comprising locating the distal tip portion 104 of the inflatable cylinder 100 at a distal end DE of the corpora cavernosum C1. Moving the second magnetic unit 114 in the distal direction attracts and moves the first magnetic unit 110 and the engaged cylinder 100 inside the corpora cavernosum C1 such that the distal tip portion 104 of the cylinder can be positioned at the distal end DE of the corpora cavernosum C1. In FIGS. 3-5, for the purpose of illustration, the second magnetic unit 114 is shown at a position distal to the first magnetic unit 110. It is to be understood that embodiments include locating the second magnetic unit 114 immediately above or around the position of the first magnetic unit 110 inside the corpora cavernosum C1.

FIG. 5 is schematic top view similar to FIGS. 3 and 4 illustrating how the method in one embodiment includes retaining the distal tip portion 104 of the inflatable penile prosthetic cylinder 100 by holding on to an exterior surface of the penis P at the distal end DE of the corpora cavernosum C1. In one embodiment, the surgeon use the thumb and index finger of one hand to provides a pressure on the penis P to retain the distal end portion 104 in the distal end DE of the corpora cavernosum C1. In one embodiment of the method, the surgeon use one hand to retain the distal end portion and the other hand (not shown) to move the second magnetic unit 114. In one embodiment, the method includes moving the second magnetic unit 114 in a proximal direction along the exterior surface of the penis P to effect moving the first magnetic unit 110 in the proximal direction inside the corpora cavernosum C1. In one embodiment, the method includes reversing the poles of the second magnetic unit 114 such that moving the second magnetic unit 114 in the proximal direction repels the first magnetic unit 110 to move the first magnetic unit 110 in the proximal direction inside the corpora cavernosum C1. In one embodiment, the method includes removing the first magnetic unit 110 through the incision I.

Figure 6:
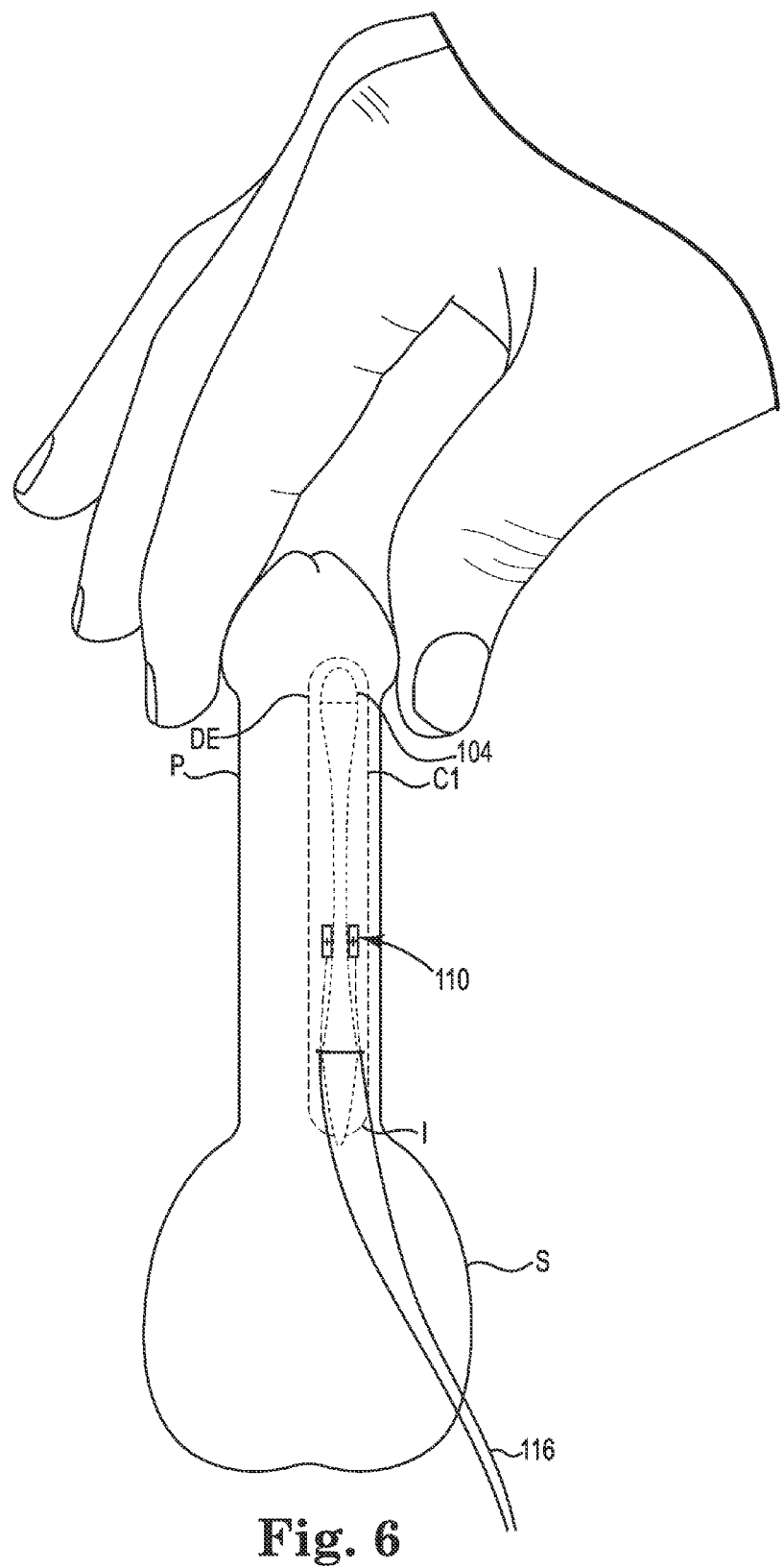
FIG. 6 is schematic top view illustrating one embodiment of the method including retaining a distal tip portion of an inflatable cylinder and moving a first magnetic unit in a proximal direction by pulling a suture.

FIG. 6 is schematic top view similar to FIGS. 3-5 illustrating how the method in an alternative embodiment includes pulling a suture 116 attached to the first magnetic unit 110 to effect moving the first magnetic unit 110 in a proximal direction inside the corpora cavernosum C1. The suture 116 extends out through the incision I and provides for the surgeon to pull the first magnetic unit 110 in the proximal direction from a position outside the penis P. In one embodiment, the method includes removing the first magnetic unit 110 through the incision I.

Figure 7:
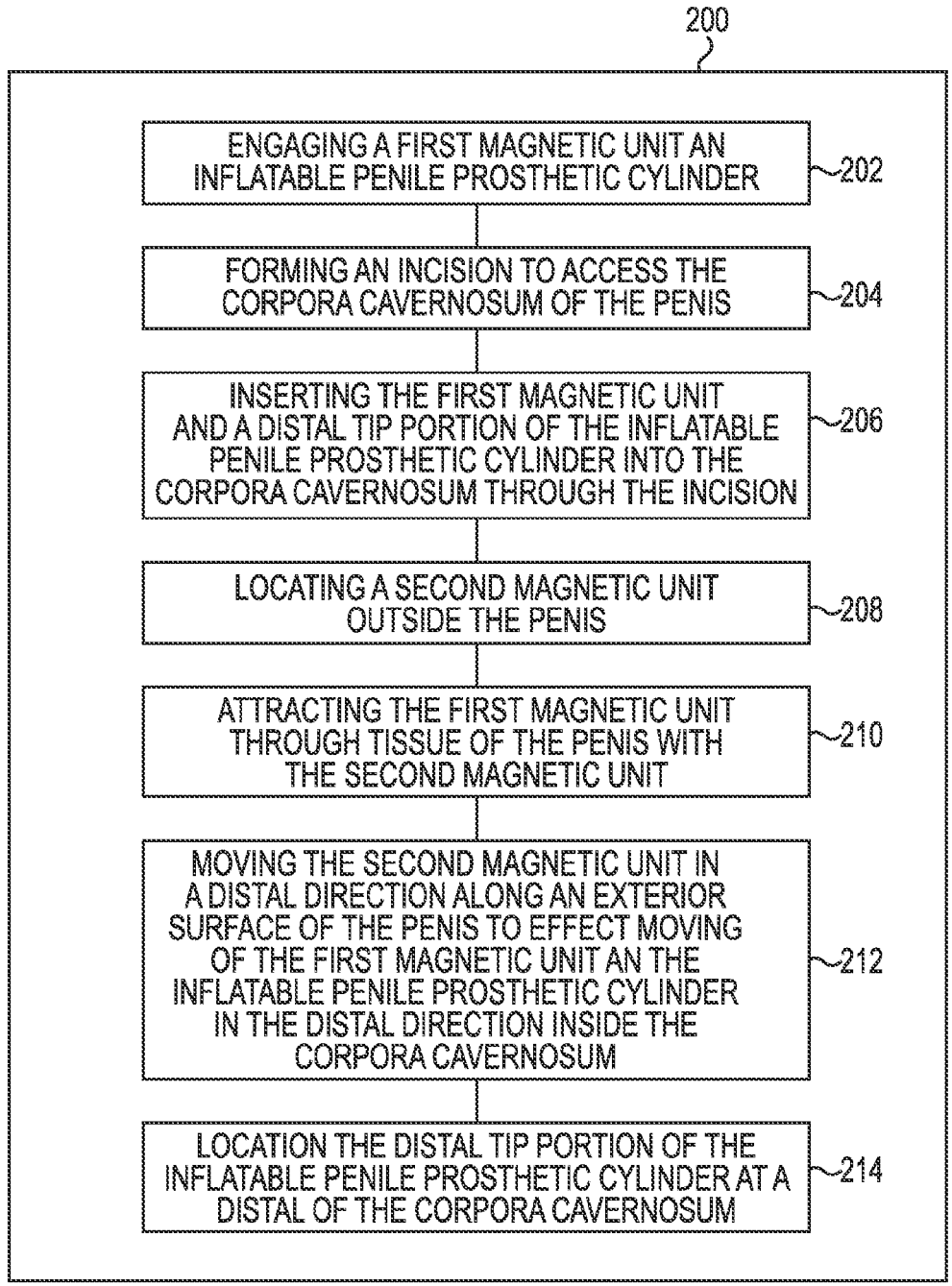
FIG. 7 is a block diagram showing one embodiment of a method for implanting a penile prosthetic insert in a corpora cavernosum of a penis.

FIG. 7 is a block diagram showing one embodiment of a method 200 for implanting a penile prosthetic insert in a corpora cavernosum of a penis. In one embodiment at 202, the method includes engaging a first magnetic unit 110 with an inflatable penile prosthetic cylinder 100. In one embodiment at 204, the method includes forming an incision to access the corpora cavernosum of the penis. In one embodiment at 206, the method includes inserting the first magnetic unit 110 and a distal tip portion 104 of the inflatable penile prosthetic cylinder into the corpora cavernosum through the incision. In one embodiment at 208, the method includes locating a second magnetic unit 114 outside the penis. In one embodiment at 210, the method includes attracting the first magnetic unit 110 through tissue of the penis with the second magnetic unit 114. In one embodiment at 212, the method includes moving the second magnetic unit 114 in a distal direction along an exterior surface of the penis to effect moving of the first magnetic unit 110 and the inflatable penile prosthetic cylinder 100 in the distal direction inside the corpora cavernosum. In one embodiment at 214, the method includes locating the distal tip portion 104 of the inflatable penile prosthetic cylinder 100 at a distal end of the corpora cavernosum.

In one embodiment, the inflatable penile prosthetic cylinder 100 is in a deflated state when it is engaged with the first magnetic unit 110.

Figure 8:
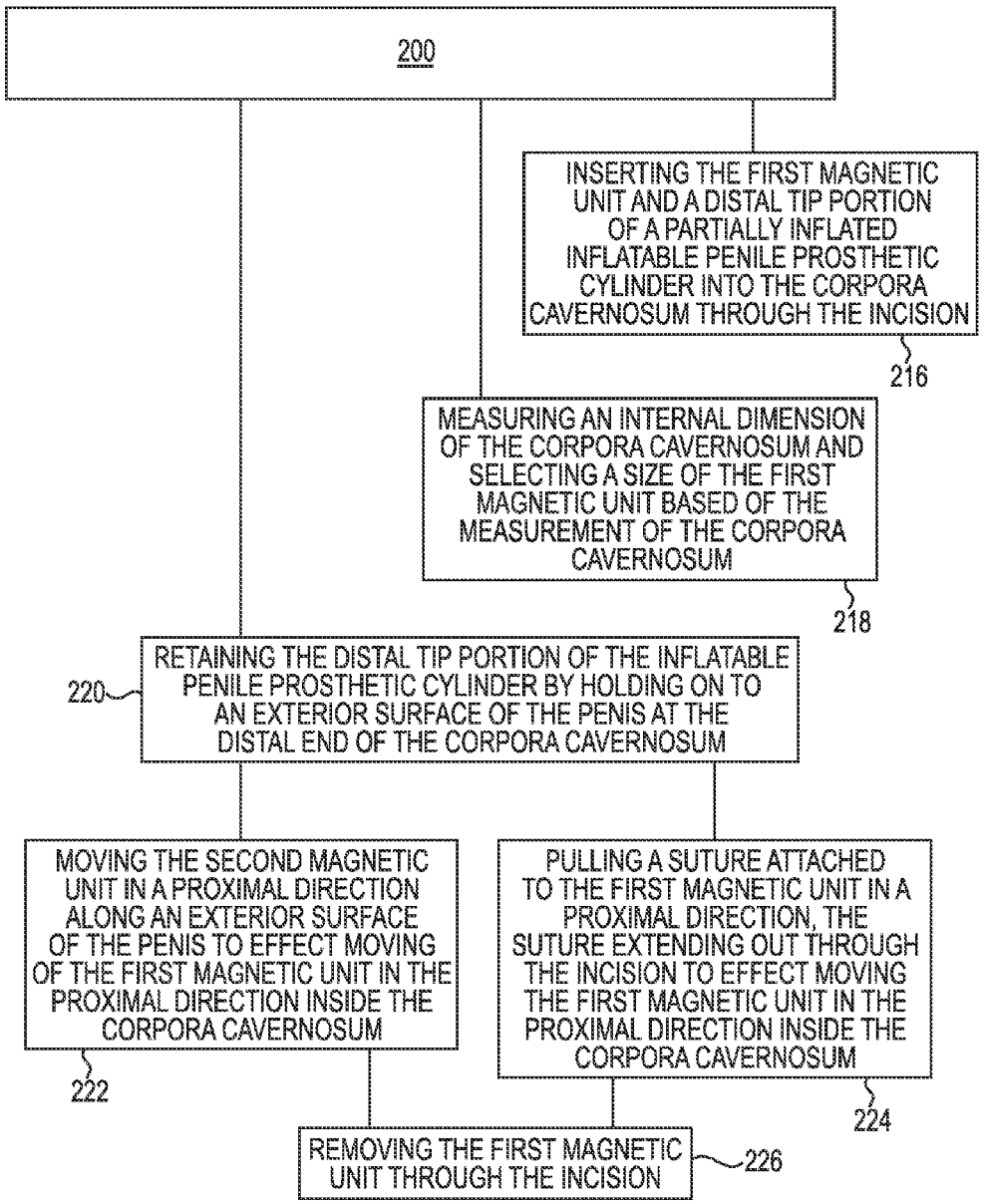
FIG. 8 is a block diagram showing embodiments of a method for implanting a penile prosthetic insert in a corpora cavernosum of a penis.

FIG. 8 is a block diagram showing embodiments of a method for implanting a penile prosthetic insert in a corpora cavernosum of a penis. In one embodiment, at 216 the method includes inserting the first magnetic unit 110 and a distal tip portion 104 of a partially inflated inflatable penile prosthetic cylinder 100 into the corpora cavernosum through the incision. In one embodiment, at 218 the method includes measuring an internal dimension of the corpora cavernosum and selecting a size of the first magnetic unit 110 based on the measurement of the corpora cavernosum. Measuring an internal dimension of the corpora cavernosum is suitably performed using a set of dilator tools, each tool configured with a stem portion and a handle portion, the stem portion of each tool in the set including a portion having a specific diameter typically provided in one millimeter increments. In a typical approach, the surgeon uses the set of dilator tools starting with the dilator of the smallest diameter, then moves on to the next size diameter until the best fitting tool is found. Based on the diameter of the best fitting dilator tool, the surgeon determines and selects an appropriate size of the inflatable cylinder 100 and in turn the size of the first magnetic unit 110 to engage with the cylinder 100 for insertion of the cylinder 100 in the corpora cavernosum. In one embodiment, at 220 the method includes retaining the distal tip portion 104 of the inflatable cylinder 100 by holding on to an exterior surface of the penis at the distal end of the corpora cavernosum. In one embodiment, at 222 the method includes moving the second magnetic unit 114 in a proximal direction along the exterior surface of the penis to effect moving the first magnetic unit 110 in the proximal direction inside the corpora cavernosum. In one embodiment, at 224 the method includes pulling a suture 116 attached to the first magnetic unit 110 in a proximal direction, the suture 116 extending out of through the incision to effect moving the first magnetic unit 110 in the proximal direction inside the corpora cavernosum. In one embodiment, at 226 the method includes removing the first magnetic unit 110 through the incision.

Figure 9:
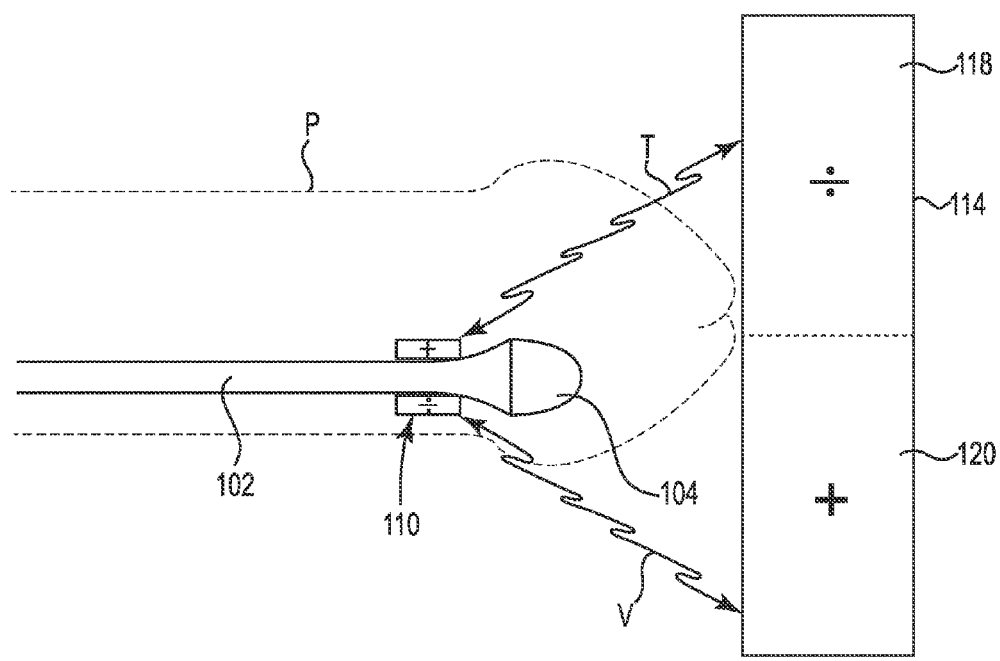
FIG. 9 is a schematic, partial cross-sectional view illustrating one embodiment of attracting a first magnetic unit with a second magnetic unit to position an inflatable penile prosthetic cylinder in a corpora cavernosum of a penis.

In one embodiment illustrated in the schematic, partial cross-sectional view of FIG. 9 showing an outline of the penis P with a dotted line, attracting the first magnetic unit 110 with the second magnetic unit 114 to move the first magnetic unit 110 and the distal end portion 104 of the cylinder 100 in the distal direction, includes positioning the second magnetic unit 114 such that both a first magnetic pole 118 and a second magnetic pole 120 of the second magnetic unit 114 attracts an opposite magnetic pole of the first magnetic unit 110. The attraction between the magnetic poles is indicated by zig-zagged two-way arrows T and V.

Figure 10A:
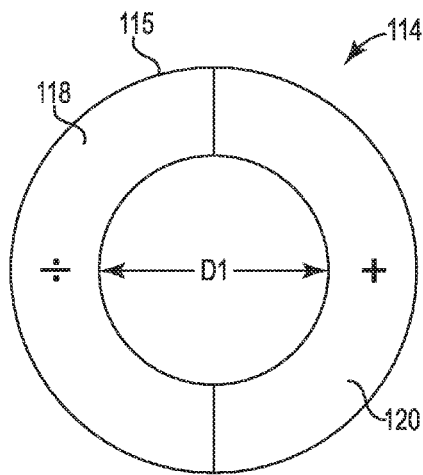
FIGS. 10A-10C illustrate embodiments of a second magnetic unit.

FIG. 10A is an end view of one configuration of a second magnetic unit 114 used in the embodiment of attracting the first magnetic unit 110 with the second magnetic unit 114 illustrated in FIG. 9. FIG. 10A shows the second magnetic unit 114 configured as a ring 115 including first magnetic pole 118 and second magnetic pole 120. The ring 115 is sized having an internal diameter D1 such that the ring 115 can locate around an outer circumference of a penis with a space between the penis and the ring 115. FIG. 10B is a top view of the second magnetic unit 114 in the form of ring 115 of FIG. 10A, showing first and second magnetic poles 118, 120.

Figure 10C:
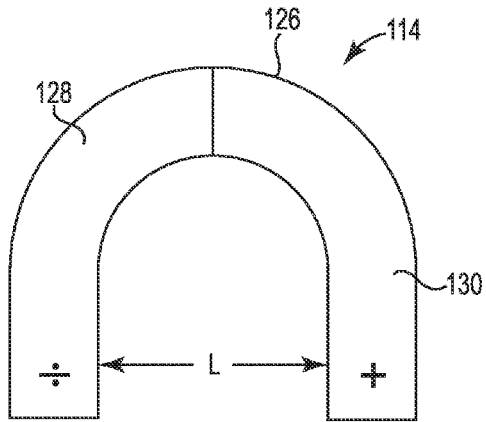
Figure 10B:
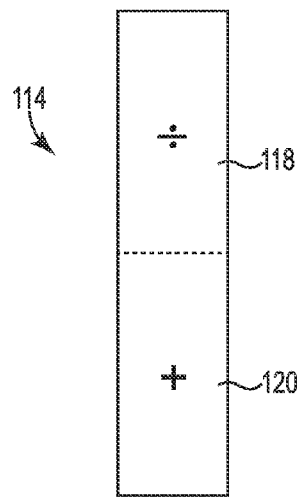

FIG. 10C is an end view of another configuration of a second magnetic unit 114 used in one embodiment of attracting the first magnetic unit 110 with the second magnetic unit 114. In FIG. 10C the second magnetic unit 114 is configured with a horseshoe-shape 126 including first magnetic pole 128 and second magnetic pole 130. A distance L between the first and second magnetic poles 128, 130 is sized such that the horseshoe-shape second magnetic unit 126 can locate around an outer width of a penis with a space between the penis and the horseshoe-shape 126.

Figure 11:
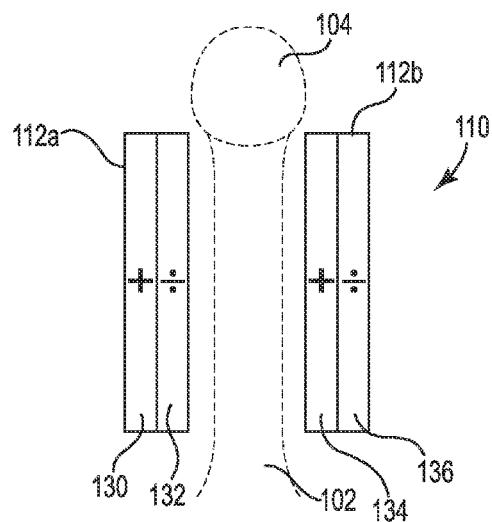
FIG. 11 illustrates one embodiment of a first magnetic unit.

FIG. 11 is a schematic top view of one configuration of a first magnetic unit 110 used in one embodiment of attracting the first magnetic unit 110 with the second magnetic unit 114 illustrated in FIG. 9. A distal tip portion 104 and a portion of the cylinder body 102 of the penile prosthetic is indicated with a dotted line to illustrate the position of the first magnetic unit 110 in one embodiment. In FIG. 11 the first magnetic unit 110 includes first and second magnet halves 112a, 112b. Each of the first and second magnet halves 112a, 112b includes first and second magnetic poles 130, 132 and 134, 136 respectively. The second magnetic pole 132 of the first magnetic half 112a attracts the first magnetic pole 134 of the second magnetic half 112b with the portion of the cylinder body 102 engaged between them. When the second magnetic unit 114 in the form of ring 115 is located at the outer surface of the penis, the first magnetic pole 130 of the first magnetic half 112a attracts to the first magnetic pole 118 of the second magnetic unit 114, and the second magnetic pole 136 of the second magnetic half 112b attracts to the second magnetic pole 120 of the second magnetic unit 114.

In embodiments, at least a part of an engagement surface of at least one of the first and second magnet halves is configured to accommodate a surface of the inflatable penile prosthetic cylinder. In one embodiment, the engagement surface of a magnet half includes a curved recess providing space in the surface of the magnet half for the cylinder material. In one embodiment, the curved recess extends between two straight surface parts that engage with similar straight surface parts on the engaging opposite magnet half. In one embodiment, the surface of the first magnetic unit engaging with an exterior surface of the inflatable cylinder are provided as an easy-slip or easy-glide surface. This helps provide for the first magnetic unit to be moved along the exterior surface of the cylinder when attracted by the second magnetic unit to effect moving the first magnetic unit.

Figure 12:
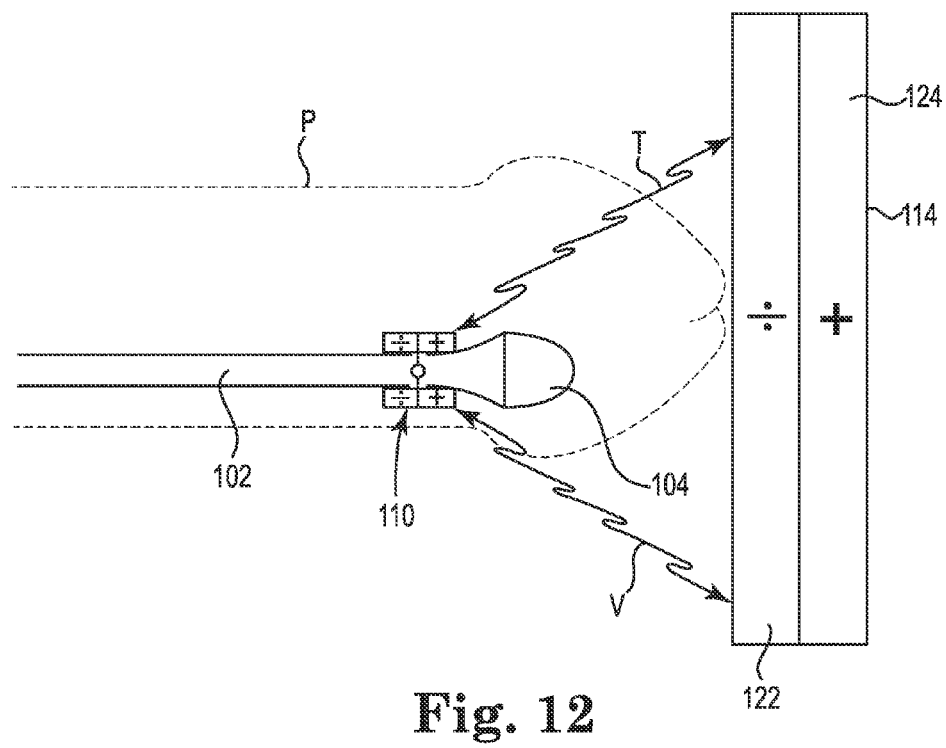
FIG. 12 is a schematic, partial cross-sectional view illustrating one embodiment of attracting a first magnetic unit with a second magnetic unit to position an inflatable penile prosthetic cylinder in a corpora cavernosum of a penis.

In one embodiment illustrated in the schematic, partial cross-sectional view of FIG. 12 showing an outline of the penis P with a dotted line, attracting the first magnetic unit 110 with the second magnetic unit 114 to move the first magnetic unit 110 and the distal end portion 104 of the cylinder 100 in the distal direction, includes attracting a single magnetic pole of the first magnetic unit 110 by a single opposite magnetic pole 122 of the second magnetic unit 114.

Figure 13A:
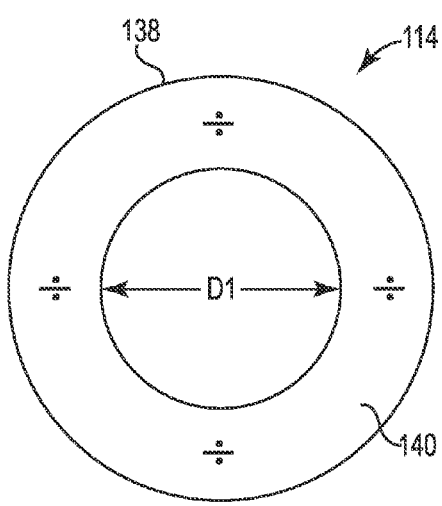
FIGS. 13A-13B illustrate embodiments of a second magnetic unit.
Figure 13B:
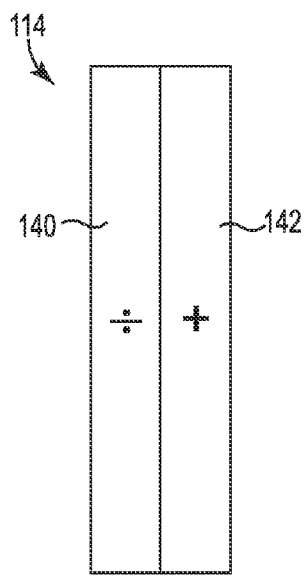

FIG. 13A is an end view of one configuration of a second magnetic unit 114 used in the embodiment of attracting the first magnetic unit 110 with the second magnetic unit 114 illustrated in FIG. 12. FIG. 13A shows the second magnetic unit 114 configured as a ring 138 with a first magnetic pole 140 facing the observer. The ring 138 is sized having an internal diameter D1 such that the ring 138 can locate around an outer circumference of a penis with a space between the penis and the ring 138. FIG. 13B is a top view of the second magnetic unit 114 in the form of ring 138 of FIG. 13A, showing the first magnetic pole 140 and a second magnetic pole 142.

Figure 14A:
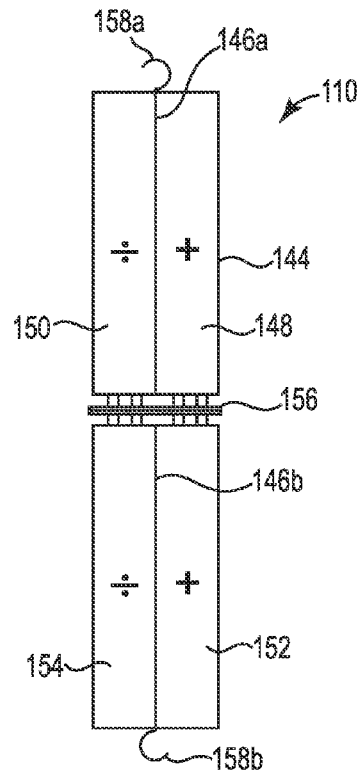
FIGS. 14A-14B illustrate embodiments of a first magnetic unit.

FIG. 14A is a schematic top view of one configuration of a first magnetic unit 110 used in one embodiment of attracting the first magnetic unit 110 with the second magnetic unit 114 illustrated in FIG. 12. FIG. 14A shows one embodiment of the first magnetic unit 110 configured as an openable brace 144. The openable brace 144 includes first and second magnet halves 146a, 146b. Each of the first and second magnet halves 146a, 146b includes first and second magnetic poles 148, 150 and 152, 154 respectively. The first magnetic half 146a is pivotally connected to the second magnetic half 146b via a pivot connection 156. One example of a suitable pivot connection 156 includes eyelets extending from each of the magnet halves 146a, 146b aligned such that a bolt or connection rod that extends through all the eyelets provides a pivot (or rotation) connection 156. The openable brace 144 includes a lock 158 having first 158a and second 158b interlockable parts. The first part 158a is attached to the first magnetic half 146a and the second part 158b is attached to the second magnetic half 146b. The lock 158 provides for the openable brace 144 to be closed around and engaged with a portion of the cylinder body 102. In one embodiment, the brace 144 is engaged around a portion of the cylinder body 102 with the first and second magnetic pole 148, 150 of the first magnetic half 146a each facing the first and second magnetic poles 152, 154 of the second magnetic half 146b having the same polarity. The lock 158 provides for the brace 144 to close around the cylinder body 102 with sufficient pressure while allowing for the brace 144 to move along an exterior surface of the cylinder 100. When the second magnetic unit 114 in the form of ring 138 is located at the outer surface of the penis, only the first magnetic pole 140 of the ring 138 attracts the first magnetic poles 148, 152 of the first and second magnet halves 146a, 146b of the first magnetic unit 110. Stated differently, a single (or one) magnetic polarity of the second magnetic unit 114 attracts a single (or one) opposite magnetic polarity of the first magnetic unit 110.

Figure 14B:
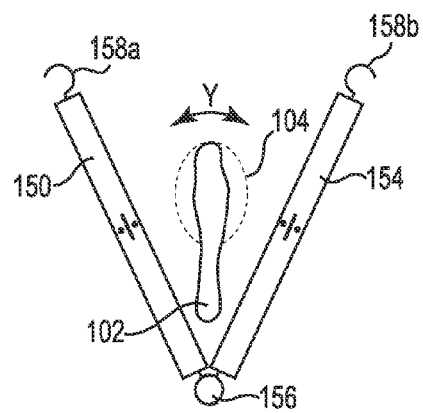

FIG. 14B is a schematic end view of the first magnetic unit 110 in the form of openable brace 144 of FIG. 14A. A distal tip portion 104 and a portion of the cylinder body 102 of the penile prosthetic are indicated, the distal tip portion 104 with a dotted line, to illustrate the position of the brace 144 proximal to the distal tip portion 104 and around the cylinder body 102 of one embodiment. Second magnetic poles 150, 154 of each of the magnet halves 146a, 146b having the same polarity face the observer. Two-way arrow Y indicates that the brace 144 can pivot at pivot connection 156 and be closed around the cylinder body 102 by first and second interlockable parts 158a, 158b.

In one aspect, the disclosure relates to a kit of parts for implanting a penile prosthetic insert in a corpora cavernosum of a penis. FIG. 15 is a top view of one embodiment of a kit of parts 300 including a packaging 302; an inflatable penile prosthetic cylinder 304; a first magnetic unit 306 configured for releasable engagement with the inflatable penile prosthetic cylinder 304; a second magnetic unit 308 configured to attract the first magnetic unit 306 through tissue of a penis and to be movable along an exterior surface of the penis, and a set of instructions for use 310 for employing the second magnetic unit 308 to deliver the first magnetic unit 306 and the inflatable penile prosthetic cylinder 304 into a corpora cavernosum of a penis.

Figure 16:
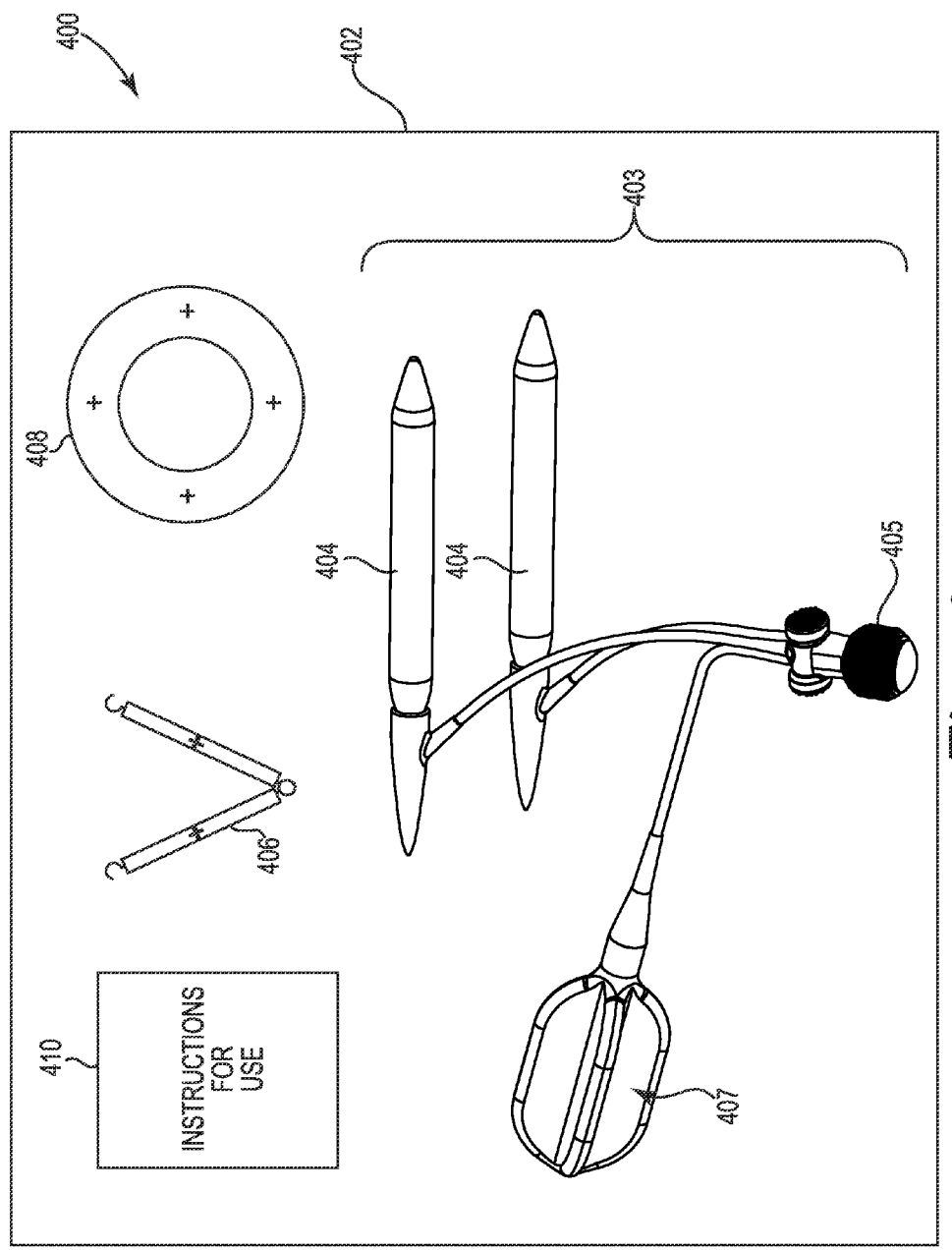
FIG. 16 is a top view of one embodiment of a kit of parts.

FIG. 16 is a top view of one embodiment of a kit of parts 400 including a packaging 402; an implantable penile prosthetic system 403 including a pump 405 attachable between a reservoir 407 and two inflatable penile prosthetic cylinders 404; a first magnetic unit 406 configured for releasable engagement with the inflatable penile prosthetic cylinder 404; a second magnetic unit 408 configured to attract the first magnetic unit 406 through tissue of a penis and to be movable along an exterior surface of the penis, and a set of instructions for use 410 for employing the second magnetic unit 408 to deliver the first magnetic unit 406 and the inflatable penile prosthetic cylinder 404 into a corpora cavernosum of a penis.

Embodiments described in this disclosure provide a method for implanting a penile prosthetic insert and a kit of parts for implanting a penile prosthetic insert. The method provides for implanting the penile prosthetic without using a sharp needle to penetrate the glans penis of the patient. The method helps provide for reduced trauma to penile tissue and thereby contributes to faster healing times to the benefit of the patient. Furthermore, the need for an introducer tool accommodating and used for bringing the sharp needle in position in the corpora cavernosum is also obviated by the method, thereby reducing procedure duration and reducing the number of entries and exits of surgical tools in and out of the corpora cavernosum.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method for implanting a penile prosthetic insert in a corpora cavernosum of a penis, the method comprising:
   engaging a first magnetic unit with an inflatable penile prosthetic cylinder;
   forming an incision to access the corpora cavernosum;
   inserting the first magnetic unit and a distal tip portion of the inflatable penile prosthetic cylinder into the corpora cavernosum through the incision; and
   locating a second magnetic unit outside the penis;
   attracting the first magnetic unit through tissue of the penis with the second magnetic unit;
   moving the second magnetic unit in a distal direction along an exterior surface of the penis to effect moving of the first magnetic unit and the inflatable penile prosthetic cylinder in the distal direction inside the corpora cavernosum; and
   locating the distal tip portion of the inflatable penile prosthetic cylinder at a distal end of the corpora cavernosum.

2. The method of claim 1, wherein the inflatable penile prosthetic cylinder is in a deflated state when it is engaged with the first magnetic unit.

3. The method of claim 1, further comprising:
partially inflating the inflatable penile prosthetic cylinder thus providing a partially inflated inflatable penile prosthetic cylinder; and
inserting the first magnetic unit and the partially inflated inflatable penile prosthetic cylinder into the corpora cavernosum through the incision.

4. The method of claim 1, further comprising measuring internal dimensions of the corpora cavernosum and selecting a size of the first magnetic unit based on the measurement of the corpora cavernosum.

5. The method of claim 1, further comprising:
retaining the distal tip portion of the inflatable penile prosthetic cylinder by holding on to an exterior surface of the penis at the distal end of the corpora cavernosum;
moving the second magnetic unit in a proximal direction along the exterior surface of the penis to effect moving the first magnetic unit in the proximal direction inside the corpora cavernosum; and
removing the first magnetic unit through the incision.

6. The method of claim 1, further comprising:
retaining the distal tip portion of the inflatable penile prosthetic cylinder by holding on to an exterior surface of the penis at the distal end of the corpora cavernosum;
pulling a suture attached to the first magnetic unit in a proximal direction, the suture extending out through the incision to effect moving the first magnetic unit in the proximal direction inside the corpora cavernosum; and
removing the first magnetic unit through the incision.

7. The method of claim 1, wherein engaging the first magnetic unit with the inflatable penile prosthetic cylinder comprises:
engaging first and second mutually attracting magnet halves with each other on opposite sides of the inflatable penile prosthetic cylinder such that a portion of the inflatable penile prosthetic cylinder is clamped between the first and second magnet halves.

8. The method of claim 1, wherein attracting the first magnetic unit with the second magnetic unit comprises positioning the second magnetic unit such that both a first and a second magnetic pole of the second magnetic unit attracts an opposite magnetic pole of the first magnetic unit.

9. The method of claim 1, wherein attracting the first magnetic unit with the second magnetic unit comprises attracting a one magnetic polarity of the first magnetic unit by one, opposite magnetic polarity of the second magnetic unit.

10. The method of claim 1, further comprising engaging additional first magnetic units with the inflatable penile prosthetic cylinder.

11. A kit of parts for implanting a penile prosthetic insert in a corpora cavernosum of a penis, the kit of parts comprising:
a packaging;
an inflatable penile prosthetic cylinder;
a first magnetic unit configured for releasable engagement with the inflatable penile prosthetic cylinder;
a second magnetic unit configured to attract the first magnetic unit through tissue of the penis and to be movable along an exterior surface of the penis; and
a set of instructions for guiding a surgeon in employing the second magnetic unit to deliver the first magnetic unit and the inflatable penile prosthetic cylinder into the corpora cavernosum.

12. The kit of parts of claim 11, wherein the first magnetic unit comprises first and second mutually attracting magnet halves.

13. The kit of parts of claim 12, wherein a part of an engagement surface of at least one of the first and second magnet halves is configured to accommodate a surface of the inflatable penile prosthetic cylinder.

14. The kit of parts of claim 11, wherein the first magnetic unit comprises an openable brace.

15. The kit of parts of claim 11, wherein the second magnetic unit is configured as a ring.

16. The kit of parts of claim 11, wherein a suture is attached to the first magnetic unit.

17. The kit of parts of claim 11, wherein each of the first and second magnetic units comprises a ferromagnetic material.

18. The kit of parts of claim 11, wherein each of the first and second magnetic units comprises a rare earth material.

19. The kit of parts of claim 11, wherein the second magnetic unit comprises an electromagnet.

20. A kit of parts comprising:
an implantable penile prosthetic system including a pump, a reservoir and two inflatable penile prosthetic cylinders, and when implanted, the pump is connected to the reservoir and to the two inflatable penile prosthetic cylinders;
a first magnetic unit configured for releasable engagement with the inflatable penile prosthetic cylinders;
a second magnetic unit configured to attract the first magnetic unit through tissue of the penis and to be movable along an exterior surface of the penis;
a set of instructions for implantation of the implantable penile prosthetic system; and
a package containing the pump, the reservoir, the two inflatable penile prosthetic cylinders, the first magnetic unit, the second magnetic unit, and the set of instructions.

* * * * *